United States Patent [19]

Sugimoto

[11] 4,419,396

[45] Dec. 6, 1983

[54] THREE-DIMENSIONAL PERFUMED SEAL

[76] Inventor: Terutaka Sugimoto, 2-20-1 Nakazato, Kita-ku, Tokyo, Japan

[21] Appl. No.: 409,102

[22] Filed: Aug. 18, 1982

[51] Int. Cl.³ .............................. A61L 9/04; G09F 3/00
[52] U.S. Cl. .................................... 428/40; 239/36; 239/56; 428/905
[58] Field of Search ................. 428/79, 28, 905, 40, 428/15; 239/34, 36, 56, 60

[56] References Cited

U.S. PATENT DOCUMENTS

| | | | |
|---|---|---|---|
| 3,334,586 | 8/1967 | Jaffa et al. | 428/909 X |
| 4,160,685 | 7/1979 | Kuroda | 428/79 X |
| 4,283,011 | 8/1981 | Spector | 428/905 X |

FOREIGN PATENT DOCUMENTS 1329309  9/1973  United Kingdom ............... 428/905

*Primary Examiner*—Henry F. Epstein
*Attorney, Agent, or Firm*—Wenderoth, Lind & Ponack

[57] ABSTRACT

A three-dimensional perfumed seal which comprises a vinyl base sheet, an adhesive layer applied to one surface of said base sheet, a release paper applied to the surface of said adhesive layer opposite from said base sheet, a foam synthetic resin padding material disposed on the surface of said base sheet opposite from said adhesive layer, a covering vinyl sheet sandwiching said padding material in cooperation with said base sheet and having a design printed on one of the opposite surfaces thereof, and a capsulated perfume layer laminated to the covering vinyl sheet at the area where said design is present.

13 Claims, 5 Drawing Figures

THREE-DIMENSIONAL PERFUMED SEAL

BACKGROUND OF THE INVENTION

This invention relates to a three-dimensional perfumed seal which comprises two opposed vinyl sheets one of which has a design printed thereon, a foam resilient padding material such as foam urethane or sponge rubber interposed between the vinyl sheets and a capsulated perfume layer laminated to the one vinyl sheet.

Of late, ornaments such as brooches and pendants, synthetic resin films and paper stickers have been increasingly impregnated with perfume so that such articles can be used not only as ornamentally appreciative articles but also as fragrant articles. However, such perfume-impregnated ornaments have the disadvantages that they are not acceptable to infants as toys and that they are expensive. And since perfume-impregnated synthetic resin films and paper stickers are flat, they have the disadvantages that the external appearance of such articles is inevitably monotonous and insipid, that they are not pleasant to the touch and that they are not suitable for being carried about.

SUMMARY OF THE INVENTION

Therefore, the present invention is to eliminate the disadvantages inherent in the prior art perfume-impregnated ornaments such as brooches and pendants, perfume-impregnated synthetic resin films and perfume-impregnated paper stickers as referred to hereinabove and for the purpose, the present invention provides a three-dimensional perfumed seal which comprises a vinyl base sheet having an adhesive layer applied to the undersurface thereof, a release paper applied to the undersurface of the adhesive layer, a foam synthetic resin padding material disposed on the upper surface of the base sheet, a covering vinyl sheet applied to the upper surface of the padding material to sandwich the padding material between the base sheet and covering sheet and having a design printed on one of the opposite surfaces of the covering sheet, said design representing a fragrant food, and a capsulated perfume layer applied to the covering sheet at the area where the design is present and containing perfume having a fragrant scent peculiar to the food represented by the design, the base sheet, adhesive layer, padding material and covering vinyl sheet being welded along the contour line of the design.

According to one aspect of the present invention, there has been provided a three-dimensional perfumed seal which comprises a vinyl base sheet, an adhesive layer applied to one surface of said base sheet, a release paper applied to the surface of said adhesive layer opposite from said base sheet, a foam synthetic resin padding material disposed on the surface of said base sheet opposite from said adhesive layer, a covering vinyl sheet sandwiching said foam padding material between said covering sheet and said base sheet and having a design printed thereon and a transparent capsulated perfume layer applied to said design on the covering vinyl sheet, said base sheet, adhesive layer, foam padding material and covering vinyl sheet being welded together along the contour line of said design.

According to another aspect of the present invention, there has been provided a three-dimensional perfumed seal which comprises a vinyl base sheet, an adhesive paper applied to the surface of said adhesive layer opposite from said base sheet, a foam synthetic resin padding material disposed on the surface of said base sheet opposite from said adhesive layer, a transparent covering vinyl sheet sandwiching said padding material between said covering sheet and said base sheet and having a design printed on the surface adjacent to said foam padding material and a transparent capsulated perfume layer laminated to said covering sheet at the area thereof opposing said design on the covering sheet, said base sheet, adhesive layer, foam padding material and covering sheet being welded together along the contour line of said design.

The above and other objects, features and attendant advantages of the present invention will be more readily apparent to those skilled in the art from a reading of the following detailed description in conjunction with the accompanying drawings which show preferred embodiments of the three-dimensional perfumed seal of the present invention for illumination purpose only, but for limiting the scope of the same in any way.

BRIEF DESCRIPTION OF THE DRAWINGS

The accompanying drawings show preferred embodiment of the three-dimensional perfumed seal of the invention in which.

DETAILED DESCRIPTION OF PREFERRED EMBODIMENTS

Figure 1:
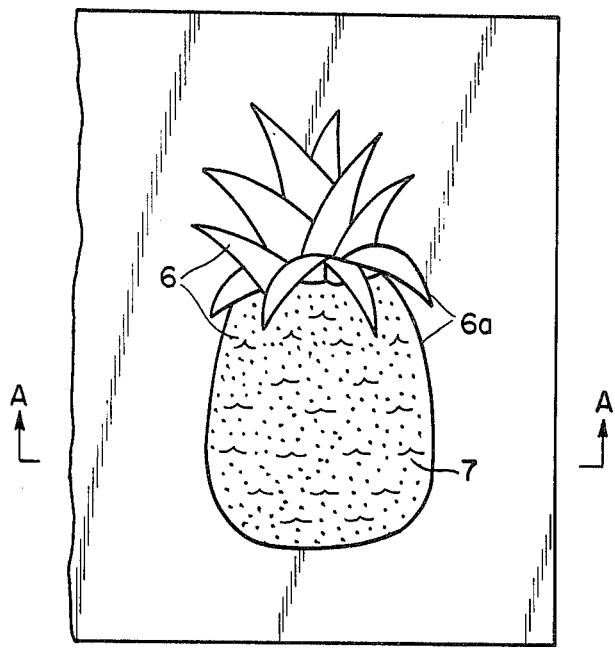
FIG. 1 is a plan view of the semiprocessed product of a first embodiment of the three-dimensional perfumed seal.
Figure 2:
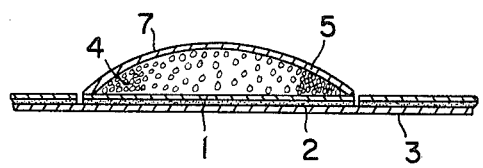
FIG. 2 is a cross-sectional view taken substantially along the line A—A of FIG.1.
Figure 3:
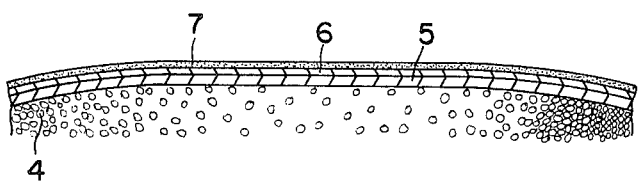
FIG. 3 is a fragmentary view on an enlarged scale of a portion of FIG. 2.

The present invention will be now described referring to the accompanying drawings and more particularly, to FIGS. 1 to 3 inclusive in which the semiprocessed product of the first embodiment of the three-dimensional perfumed seal of the present invention is shown.

The semiprocessed product of the three-dimensional seal generally comprises a vinyl base sheet or substrate 1, an adhesive layer 2 applied to the undersurface of the base sheet 1, a release paper 3 applied to the undersurface of the adhesive layer 2, a foam resilient padding material 4 disposed on the upper surface of the base sheet 1 and a covering vinyl sheet 5 applied to the upper surface of the padding material 4 to sandwich the padding material 4 therebetween. The outer surface of the covering sheet 5 has a design 6 printed thereon and the design 6 represents a food such as a fruit (the design represents a pineapple in the illustrated embodiment). A transparent capsulated perfume layer 7 is laminated to the entire area or a portion of the covering sheet 5 and the capsulated perfume layer comprises a plurality of capsules formed of high molecular compound connected together by a binder and each containing a predetermined amount of perfume therein. The capsulated perfume layer 7 is laminated to the covering sheet 5 by a screen printing process. The perfume to be capsulated in the capsules should be selected depending upon the design 6 printed on the covering sheet 5, that is, the perfume should be that emitting the scent peculiar to the food represented by the design 6 printed on the covering sheet 5. The base sheet 1, adhesive layer 2, padding material 4 and covering sheet 5 are cut and welded together along the contour line 6a of the design 6 by a high frequency welder to thereby obtain a desired three-dimensional perfumed seal.

Figure 4:
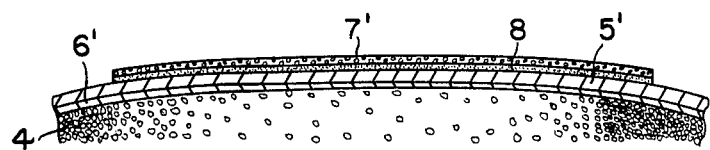
FIG. 4 is similar to FIG. 3, but shows the semiprocessed product of a second embodiment of the three-dimensional perfumed seal of the invention.

Referring now to FIG. 4 of the accompanying drawings in which a modification of the semiprocessed product of the three-dimensional seal of the invention is illustrated, the modified semiprocessed product is substantially similar to the preceding embodiment except for the covering vinyl sheet and the provision of an undercoating on the upper surface of the covering vinyl sheet. In the modified embodiment of FIG. 4, the covering vinyl sheet 5' is formed of a transparent lustrous vinyl sheet and has a design 6' printed on the inner surface thereof so that the design 6' can be seen on the outer surfaces of the covering sheet 5 and capsulated perfume layer 7 through the covering sheet and perfume layer as a lustrous design. In the modified embodiment, since the outer surface of the covering sheet 5 is lustrous and the printing ink of the design 6' is not present on the vinyl sheet outer surface, the capsulated perfume layer 3 can not be easily luminated to the covering vinyl sheet 5. Thus, in the modified embodiment of FIG. 4, an undercoating 8 of transparent ink compatible with vinyl is applied to the outer surface of the covering vinyl sheet 5' at the area thereof opposing the design 6' on the inner surface of the sheet and the capsulated perfume layer 7 is laminated to the undercoating 8 by the screen printing process.

As mentioned hereinabove, since the padding 4 of foam urethane or sponge rubber is interposed between the base sheet 1 and covering vinyl sheet 5, the obtained perfumed seal is a decorative article having a three-dimensional appearance and a resiliency and the lamination of the capsulated perfume layer 7 on the covering vinyl sheet directly or through the undercoating 8 is a novel feature of the present invention.

Although the perfume normally does not emit its fragrant scent because it is capsulated, when a portion of the capsulated perfume layer 7 is rubbed or scratched by a human finger nail or tip, the capsule or capsules which are present in the rubbed or scratched portion of the capsulated perfume layer 3 tear and the perfume contained in the torn capsule or capsules emits its fragrant scent. Thus, according to the present invention, as mentioned hereinabove, since the capsulated perfume is that having the same scent as that peculiar to the food represented by the design 6 or 6' on the covering sheet 5 (the pineapple is illustrated in FIG. 1), the perfume contained in the torn capsule or capsules emits the very scent represented by the design 6 or 6' on the covering sheet 5. Furthermore, since the foam resilient padding material 4 is interposed between the base sheet 1 and covering sheet 5 or 5', the covering sheet 5 or 5' is caused to bulge outwardly or away from the base sheet 1 so that a human finger or nail tip can positively access to the capsulated perfume layer 7 and gives a moderately resilient touch to the seal so that a human finger or nail tip can closely contact the capsulated perfume layer 7 and thus, even an infant can use the seal without difficulties.

And since the adhesive layer 2 is applied to the undersurface of the base sheet 1 and releasably held on the release sheet 3, the seal can be easily separated from the release sheet 3 and applied to a bag, satchel or apparel to be carried about. Alternatively, the seal can be also applied to a stationary support structure such as wall or pillar as desired and in such a case the user's nostril can access to the capsulated perfume layer.

Figure 5:
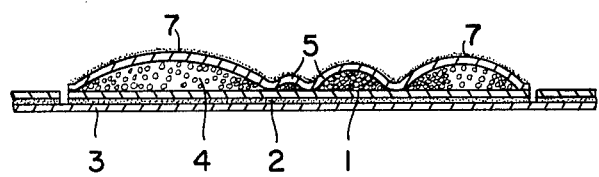
FIG. 5 is a cross-sectional view of the semiprocessed product of a third embodiment of the three-dimensional perfumed seal of the invention.

Although the covering sheet 5 or 5' is shown as having a dome-shaped configuration in FIGS. 2 to 4 inclusive, the covering sheet may have an undulated configuration as shown in FIG. 5 within the scope of the present invention.

The modified semiprocessed products of FIGS. 4 and 5 are also cut along the contour lines of the designs by a high frequency welder in the same manner as described in connection with FIGS. 1 to 3 inclusive to obtain desired three-dimensional perfumed seals.

In the foregoing, description has been made of specific embodiments of the present invention, but it will be readily occur to those skilled in the art that the same are illustrative in nature, but do not limit the scope of the invention in any way. The scope of the invention is only limited by the appended claims.

What is claimed is:

1. A three-dimensional perfumed seal, suitable for use by infants, comprising a vinyl base sheet, an adhesive layer applied to one surface of said base sheet, a release paper applied to the surface of said adhesive layer opposite from said base sheet, a foam synthetic resin padding material disposed on the surface of said base sheet opposite from said adhesive layer, a covering vinly sheet sandwiching, said foam padding material between said covering sheet and said base sheet and said covering vinyl sheet bulging outwardly from said base sheet over the entire length thereof and having a design printed thereon and a transparent capsulated perfume layer applied to said design on the covering vinyl sheet, said base sheet, adhesive layer, foam padding material and covering vinyl sheet being welded together along the contour line of said design.

2. The three-dimensional perfumed seal as set forth in claim 1, in which said design is printed on the outer surface of the covering vinyl sheet.

3. The three-dimensional perfumed seal as set forth in claim 1, in which said foam synthetic resin padding material is foam urethane rubber.

4. The three-dimensional perfumed seal as set forth in claim 1, in which said foam synthetic resin padding material is foam sponge rubber.

5. The three-dimensional perfumed seal as set forth in claim 1, in which said design on the covering vinyl sheet represents a fruit.

6. The three-dimensional perfumed seal as set forth in claim 1, in which said capsulated perfume layer comprises a plurality of transparent capsules connected together and secured to said design on the covering vinyl sheet by binder and each containing a predetermined amount of perfume therein.

7. The three-dimensional perfumed seal as set forth in claim 1, in which said covering vinyl sheet has a dome-shaped configuration.

8. The three-dimensional perfumed seal as set forth in claim 1, in which said covering vinyl sheet has an undulated configuration.

9. A three-dimensional perfumed seal, suitable for use by infants, comprising a vinyl base sheet, an adhesive layer applied to one surface of said base sheet, a release paper applied to the surface of said adhesive layer opposite from said base sheet, a foam synthetic resin padding material disposed on the surface of said base sheet opposite from said adhesive layer, a transparent covering vinyl sheet sandwiching said padding material between said covering sheet and said base sheet, said covering vinyl sheet, bulging outwardly from said base sheet over the entire length thereof and having a design printed on the surface adjacent to said foam padding material and a transparent capsulated perfume layer laminated to said covering sheet at the area thereof opposing said design on the covering sheet, said base sheet, adhesive layer, foam padding material and covering vinyl sheet being welded together along the contour line of said design.

10. The three-dimensional perfumed seal as set forth in claim 9, in which said foam synthetic resin padding material is foam urethane rubber.

11. The three-dimensional perfumed seal as set forth in claim 9, in which said foam synthetic resin padding material is foam sponge rubber.

12. The three-dimensional perfumed seal as set forth in claim 9, in which said design on the covering sheet represents a fruit.

13. The three-dimensional perfumed seal as set forth in claim 9, in which said capsulated perfume layer comprises a plurality of transparent capsules connected together and secured to said covering vinyl sheet by binder and each containing a predetermined amount of perfume therein.

* * * * *